US011485988B2

(12) United States Patent
Björklund et al.

(10) Patent No.: US 11,485,988 B2
(45) Date of Patent: *Nov. 1, 2022

(54) METHOD FOR COOLING AND DETOXIFYING BIOMASS

(71) Applicant: Valmet AB, Sundsvall (SE)

(72) Inventors: Peter Björklund, Umeå (SE); Andreas Averheim, Sundsvall (SE)

(73) Assignee: VALMET AB, Sundsvall (SE)

( * ) Notice: Subject to any disclaimer, the term of this patent is extended or adjusted under 35 U.S.C. 154(b) by 0 days.

This patent is subject to a terminal disclaimer.

(21) Appl. No.: 16/952,311

(22) Filed: Nov. 19, 2020

(65) Prior Publication Data

US 2022/0154233 A1 May 19, 2022

(30) Foreign Application Priority Data

Jan. 8, 2020 (EP) .................................. 20150733

(51) Int. Cl.
| | | |
|---|---|---|
| *D21C 7/00* | (2006.01) | |
| *D21C 3/24* | (2006.01) | |
| *D21C 5/00* | (2006.01) | |
| *C12P 19/00* | (2006.01) | |
| *C12P 19/02* | (2006.01) | |
| *C12P 19/14* | (2006.01) | |
| *C13K 1/02* | (2006.01) | |
| *D21C 7/06* | (2006.01) | |
| *D21C 7/08* | (2006.01) | |
| *D21C 7/10* | (2006.01) | |

(52) U.S. Cl.
CPC ............... *C12P 19/02* (2013.01); *C12P 19/14* (2013.01); *C13K 1/02* (2013.01); *D21C 5/005* (2013.01); *D21C 7/06* (2013.01); *D21C 7/08* (2013.01); *D21C 7/10* (2013.01)

(58) Field of Classification Search
CPC ................ C13K 1/00; C10L 5/44; C10L 9/08
See application file for complete search history.

(56) References Cited

U.S. PATENT DOCUMENTS

| | | | |
|---|---|---|---|
| 9,284,382 B2 * | 3/2016 | Chen .......................... C08B 1/00 |
| 2009/0098616 A1 | 4/2009 | Burke et al. |
| 2009/0098617 A1 | 4/2009 | Burke et al. |
| 2012/0111515 A1 | 5/2012 | Nilsen et al. |
| 2012/0115200 A1 | 5/2012 | Dottori et al. |
| 2016/0069020 A1 | 3/2016 | Dottori et al. |
| 2018/0355303 A1 | 12/2018 | Rowland et al. |
| 2019/0194697 A1 | 6/2019 | Dechman et al. |
| 2020/0332375 A1 * | 10/2020 | Bjorklund ............... C10L 5/361 |
| 2021/0340487 A1 * | 11/2021 | Pettersson ............... C12P 19/02 |

OTHER PUBLICATIONS

Extended European Search Report for European Application No. 20150733.2 dated Jul. 16, 2020 (6 pages).
Extended European Search Report for European Application No. 20150723.3 dated Aug. 28, 2020 (7 pages).

* cited by examiner

*Primary Examiner* — Maryam Monshipouri
(74) *Attorney, Agent, or Firm* — Morgan, Lewis & Bockius LLP (57) ABSTRACT

The present invention relates to an improved method and device for treating biomass in which thermally treated biomass is discharged from a pressurized reactor and introduced into a blow tank and then a flash tank, wherein the absolute pressure in the blow tank is maintained above atmospheric pressure and the absolute pressure in the flash tank is maintained below atmospheric pressure. The slurry of biomass separated in the flash tank is then enzymatically treated. The heat from the thermally treated biomass is recovered from the latent heat of a vaporous aqueous stream withdrawn from the blow tank.

20 Claims, 3 Drawing Sheets

METHOD FOR COOLING AND DETOXIFYING BIOMASS

FIELD OF THE INVENTION

The present invention relates to an improved method and device for treating biomass in which thermally treated biomass is discharged from a pressurized hydrolysis reactor into a blow tank wherein the absolute pressure is maintained above atmospheric pressure to facilitate recovery of secondary heat as low-pressure steam. The hydrolyzed biomass is further cooled and detoxified by flash evaporation for further treatment with for example enzymes.

BACKGROUND ART

It is known in the art to pre-hydrolyze biomass sugars in a reactor in which hemicellulose sugar is dissolved from biomass at elevated temperature and pressure, optionally in the presence of an acidic catalyst. With biomass is here meant any type of lignocellulosic material which contains hydrolysable hemicellulose or cellulose sugar. The acidic catalyst is preferably selected from sulfuric acid, acetic acid or sulphur dioxide as gas or dissolved in water to sulphurous acid. The temperature in the reactor is typically around 200° C. and the pressure is in the range 15 to 20 bar. There is not necessary a free liquid level in the reactor, but the biomass comprises a certain amount of moisture. The reactor is discharged after completed sugar hydrolysis to an atmospheric receiving container, in the following called a "blow tank". The temperature of the discharge, which contains mainly biomass, hydrolyzed sugar and water, drops rapidly to about 100° C. when water and other volatile compounds evaporate to equilibrium to the pressure prevailing in the blow tank. Said pre-hydrolyzed biomass may be then hydrolyzed enzymatically further to release cellulosic sugar. The released sugar is fermented to ethanol, fodder yeast or used as feed stock for various platform chemicals.

The pre-hydrolyzed biomass must be cooled typically to about 40-60° C. and it must be diluted to 10-20% insoluble material content to secure a good activity in downstream enzymatic hydrolysis and/or fermentation steps. It is known in the art to cool and dilute hydrolyzed biomass by mixing it to a slurry with a cold or cooled coolant for example water, a recycled process condensate or a recycled process filtrate. Additionally, the pH of the pre-hydrolyzed slurry must be adjusted to a pH range 4.0 to 6.5 for good enzymatic activity. Said method of cooling by mixing coolant to the pre-hydrolyzed biomass may result in dilution of the slurry below 10% which has the drawback of suboptimal conditions with high operation cost, because the dilution liquid will be removed in downstream process stages. In addition, the diluted slurry contains carboxylic acids and furfural, which are toxic and reduce activity of enzymes and yeast in the enzymatic hydrolysis and fermentation steps.

EP 3212764 B1 discloses a method for thermal hydrolysis where biomass is discharged from a pressurized pre-hydrolysis reactor by steam explosion into one or more atmospheric pressure relief tank(s). The discharged biomass has a temperature of 95-110° C. and is processed to ethanol, hydrogen, lactic acid, methane organic acids or other desired produced by fermentation at a pH of 7-8.5. The invention teaches to dilute and cool the hydrolyzed biomass by recycling cooled liquid from downstream digestion to the pressure relief tank(s). Said invention further teach to recover secondary of heat from steam withdrawn from the pressure relief tank(s) with a direct condenser with or without a recycle cooler.

EP 18 208 026.7 discloses a method for treating biomass in which thermally treated biomass is discharged from a pressurized pre-hydrolysis reactor unit and dewatered followed by cooling of the separated liquid phase. Said invention teaches us to install a dewatering press or alike to separate hot hydrolysate before cooling it with a heat exchanger. The cooled hydrolysate is then back-mixed with the dewatered biomass which is pumped to enzymatic hydrolysis. The inventors claim that problems with scaling and plugging of cooling heat-exchangers may be reduced with their invention.

US 2015/0232902 A1 describes a method of cooling a thermally hydrolyzed biomass prior to mixing it with enzymes. Said patent teach us to split the enzymatic hydrolysis in two steps such that the first enzymatic hydrolysis step operates with a shortened duration (small reactor volume) and the second enzymatic step(s) operates with long duration (large reaction volume to provide completed saccharification). The duration of the first reactor is such that it saccharifies (liquefies) cellulose enough to provide a pumpable water (hydrolysate) solution through a recycle cooler (heat exchanger). This way it is no longer necessary to recycle coolant (hydrolysate) over the second enzymatic step. The inventors claim that the total (first and second) reaction volume is much smaller in comparison to having only one enzymatic reaction volume.

EP 2958978 B1 teach us a method of recovery of heat from a batch type steam explosion process. Handling of un-condensed gas from steam explosion system is required from environmental (air protection) reasons, but it is very demanding from control point of view in a batch process. The method comprises a heat exchanger for condensing and a gas-holder with flexible volume for equalizing the volume flow of un-condensed gas to a treatment process.

Biomass hydrolysis followed by steam explosion is a thermal treatment process. The energy is provided by medium pressure steam which heats the biomass to the processing temperature and assists in discharging hydrolyzed biomass from the pressurized rector to the blow tank. The steam usage in the reactor, which depends on material moisture and steam loss at discharging, is typically in the range 0.4-1.5 ton per each ton of dry biomass. This steam usage represents a significant part of the operating cost of biomass hydrolysis and it may be reduced if the process is furnished with recovery of secondary heat, i.e. recovery of steam when biomass evaporates to equilibrium at discharge to the blow-tank. Condensing heat is available at 100° C. at the highest since the pressure in the blow tank is atmospheric. Recovered heat may be used for example for production of hot water in condenser or for pre-heating of biomass to hydrolysis.

There is still a need for an improved method and device for cooling thermally treating biomass to a temperature range of optimum enzymatic activity, which is typically about 40 to 60° C., which avoids diluting the thermally treating biomass with a cooling liquid and recovering the heat of the thermal treatment process. Additionally, the problems of adjusting the pH to the pH range of optimum enzymatic activity of 4.0 to 6.5, without further diluting the thermally treating biomass and the presence of toxic components like carboxylic acids and furfural in the pretreated biomass slurry are not solved.

SUMMARY OF THE INVENTION

The present invention relates to a method for treating biomass comprising the steps of (a) feeding lignocellulosic biomass to a pressurized reactor;
(b) supplying steam to the pressurized reactor and at least partially condensing said steam in the pressurized reactor;
(c) hydrolysing hemicellulose sugars of said biomass with said at least partially condensed steam in the pressurized reactor;
(d) discharging said hydrolyzed biomass from the pressurized reactor into a blow tank by steam explosion to produce a steam exploded biomass;
(e) diluting the steam exploded biomass in the blow tank with an aqueous diluent to a pumpable aqueous slurry;
(f) pumping said aqueous slurry from the blow tank to a flash-tank for evaporative cooling to produce a cooled aqueous slurry;
(g) discharging the cooled aqueous slurry from the flash tank as discharged cooled aqueous slurry stream;
(h) treating the discharged cooled aqueous slurry stream with an enzyme;
characterized by
    withdrawing a first vaporous aqueous stream from the blow tank for maintaining the absolute pressure in the blow tank above the atmospheric pressure;
    recovering the latent heat from the first vaporous aqueous stream; and
    withdrawing a second vaporous aqueous stream from the flash tank for maintaining the absolute pressure in the flash tank below the atmospheric pressure.

Further, the present invention relates to a device for treating biomass comprising
    a biomass feeding system;
    a pressurized reactor for thermally treating the biomass
    a blow tank;
    a discharging system for discharging the hydrolyzed biomass from the pressurized reactor to the blow tank by steam explosion;
    a flash tank; and
    a unit for enzymatically treating treated cooled aqueous slurry stream of biomass discharged from the flash tank;
wherein
the blow tank comprises
    means for maintaining the absolute pressure in the blow tank above atmospheric pressure, preferably above 2 bar (a), still more preferably above 3 bar(a) and most preferably from 4 to 8 bar (a);
    at least one injection port for injecting an aqueous diluent;
    at least one discharge port for discharging a first vaporous aqueous stream;
    at least one discharge port for discharging an aqueous slurry stream comprising the steam exploded biomass;
the flash tank comprises
    means for maintaining the absolute pressure in the flash tank below atmospheric pressure, preferably below 0.5 bar (a), still more preferably below 0.3 bar(a) and most preferably from 0.01 to 0.25 bar (a);
    at least one discharge port for discharging a second vaporous aqueous stream;
    at least one discharge port for discharging a cooled aqueous slurry stream, and the device further comprises a unit for recovering the latent heat from said first vaporous aqueous stream withdrawn from the blow tank.

Definitions

Biomass is any source of plant material suitable for converting into pulp and paper material, cellulose-based construction material or biofuel. Suitable sources of biomass are lignocellulosic biomass such as virgin biomass, waste biomass and energy crops. Virgin biomass includes all naturally occurring terrestrial plants such as trees, bushes and grass. Waste biomass is produced as a low-value byproduct of various industrial sectors such as agriculture, e.g. selected from corn stover, sugarcane bagasse, straw etc., and forestry, e.g. selected from saw mill and paper mill discards. Energy crops are crops with high yield of lignocellulosic biomass produced to serve as a raw material for production of second generation (2G) biofuel. Examples include switch grass (*Panicum virgatum*) and elephant grass.

In the present invention lignocellulosic biomass is used. The terms "lignocellulosic biomass" and "biomass" are used exchangeably.

DETAILED DESCRIPTION

Method

The present invention relates to a method for treating biomass comprising the steps of
(a) feeding lignocellulosic biomass to a pressurized reactor;
(b) supplying steam to the pressurized reactor and at least partially condensing said steam in the pressurized reactor;
(c) hydrolysing hemicellulose sugars of said biomass with said at least partially condensed steam in the pressurized reactor;
(d) discharging said hydrolyzed biomass from the pressurized reactor into a blow tank by steam explosion to produce a steam exploded biomass;
(e) diluting the steam exploded biomass in the blow tank with an aqueous diluent to a pumpable aqueous slurry;
(f) pumping said aqueous slurry from the blow tank to a flash-tank for evaporative cooling to produce a cooled aqueous slurry;
(g) discharging the cooled aqueous slurry from the flash tank as discharged cooled aqueous slurry stream;
(h) treating the discharged cooled aqueous slurry stream with an enzyme;
characterized by
    withdrawing a first vaporous aqueous stream from the blow tank for maintaining the absolute pressure in the blow tank above the atmospheric pressure;
    recovering the latent heat from the first vaporous aqueous stream; and
    withdrawing a second vaporous aqueous stream from the flash tank for maintaining the absolute pressure in the flash tank below the atmospheric pressure.

Before feeding the biomass into the pressurized reactor the biomass can be pretreated by cutting and/or washing.

The biomass can additionally be pretreated by dilute acid hydrolysis by contacting with a dilute solution containing an external acidic catalyst, reinforced autohydrolysis by contacting with a dilute solution containing a recirculated acidic catalyst or autohydrolysis by contacting with water. The external or recirculated acidic catalyst is preferably selected from sulfuric acid, acetic acid or sulphur dioxide as gas or dissolved in water to sulphurous acid. These pretreatment measures are well known in the art.

In one embodiment the biomass fed into the pressurized reactor is preferably a solid dry material.

In another embodiment the biomass fed into the pressurized reactor is preferably an aqueous slurry of biomass.

The biomass is preferably fed into the pressurized prehydrolysis reactor unit by means of a feeding system. The feeding system preferably comprises means for actively conveying the biomass into the pressurized prehydrolysis reactor unit such as a screw feeder, e.g. a plug screw feeder optionally with a force feed screw feeding the plug screw feeder.

Suitable means for actively conveying the biomass into the pressurized reactor are known in the art.

The pressurized reactor can comprise one or more such as one or two reactors.

In one embodiment the pressurized reactor comprises more than one reactor such as two reactors. If the pressurized reactor comprises more than one reactor, e.g. an impregnation reactor and a hydrolysis reactor, the reactors are usually arranged in series. For example, biomass can be fed into an impregnation reactor and then be impregnated in the impregnation reactor. In the impregnation reactor the biomass is usually impregnated by dilute acid hydrolysis by contacting with a dilute solution containing an external acidic catalyst, reinforced autohydrolysis by contacting with a dilute solution containing a recirculated acidic catalyst or autohydrolysis by contacting with water. The external or recirculated acidic catalyst is preferably selected from sulphuric acid, acetic acid or sulphur dioxide as gas or dissolved in water to sulphurous acid. Afterwards, the biomass can be discharged from the impregnation reactor and fed to the subsequent respectively downstream hydrolysis reactor. The pressurized reactor can also comprise two or more hydrolysis reactors arranged in series and operating at same or different temperature and pressure.

In the hydrolysis reactor the biomass is thermally treated preferably in the presence of water under pressure, more preferably by heating with steam, to produce a thermally treated biomass. In particular, the biomass can be exposed to steam in the hydrolysis reactor, wherein the steam is fed into the hydrolysis reactor in addition to the biomass. By exposing the biomass to steam, the biomass is pressurized in the hydrolysis reactor, and steam is at least partially condensed.

In contact with said at least partially condensed steam the hemicellulose sugars of the biomass are hydrolyzed so that a hydrolyzed biomass is obtained in the hydrolysis reactor.

In another embodiment the pressurized reactor comprises only one reactor which suitably is a prehydrolysis reactor. In said single hydrolysis reactor the biomass is thermally treated and hydrolyzed in the presence of at least partially condensed steam as discussed above. In one embodiment the biomass is additionally impregnated in said single hydrolysis reactor as discussed above.

It is preferred that the biomass is thermally treated in the pressurized reactor, preferably the hydrolysis reactor at a pressure of 5 to 35 bar(a), more preferably 10 to 25 bar(a), and most preferably of 15 to 20 bar(a).

The thermally treated biomass in the pressurized reactor, preferably the hydrolysis reactor is preferably heated to a temperature of from 120° C. to 250° C., preferably from 150° C. to 220° C. and most preferably from 170° C. to 215° C.

The hydrolysis reactor can be a vertical hydrolysis reactor or a horizontal hydrolysis reactor. Vertical and horizontal hydrolysis reactors are generally known in the art.

The residence time of the thermally treated biomass in the pressurized prehydrolysis reactor unit is preferably in the range of from 1 to 30 minutes, more preferably from 3 to 15 minutes, and most preferably from 5 to 10 minutes.

The hydrolyzed biomass is discharged from the pressurized reactor, for example in a blow valve or restriction, which may have the shape of a hole, arranged downstream the pressurized reactor.

The hydrolyzed biomass is discharged through steam explosion. The steam explosion is defined as a rapid pressure decrease leading to a flashing of the steam. By means of steam explosion the fibers of the biomass disrupted to improve the accessibility of the carbohydrates, such as cellulose and hemicellulose, for subsequent processes, such as enzymatic hydrolysis. Steam explosion is a technique well known in the art of biomass pretreatment.

Before being discharged from the pressurized reactor the hydrolyzed biomass in the pressurized reactor preferably has a temperature of from 120° C. to 250° C., more preferably from 160° C. to 230° C. and most preferably from 180° C. to 220° C.

When discharging the hydrolyzed biomass through steam explosion the weight amount of the biomass in the discharged hydrolyzed biomass is preferably in the range of from 25 to 60 wt %, more preferably in the range of from 30 to 55 wt %, and most preferably in the range of from 40 to 55 wt %, based on the total weight of the hydrolyzed biomass.

Steam explosion is especially effective for the pretreatment of agricultural residues and hardwood.

The hydrolyzed biomass is discharged from the pressurized reactor by steam explosion into a blow tank, wherein the absolute pressure in the blow tank is maintained above atmospheric pressure.

Preferably the absolute pressure in the blow tank is maintained below above 2 bar (a), still more preferably above 3 bar(a) and most preferably from 4 to 8 bar (a), such as 6 bar (a).

It is preferred that the hydrolyzed biomass is directly discharged from the pressurized prehydrolysis reactor unit into the blow tank.

The discharge from the reactor which operates at high pressure into the blow tank is violent. Part of the moisture contained in the pores of the biomass will evaporate to steam due to the decreased pressure. The steam expands and breaks the biomass structure. Also, mechanical effects (impact, friction), caused by high velocity during the discharge contribute to disintegration of the biomass.

Evaporated water (blow steam) and hydrolyzedsteam exploded biomass are preferably separated in the blow tank in two separate streams, a first vaporous aqueous stream and an aqueous slurry comprising the steam exploded biomass.

It is preferred that the two streams are separated by means for separating a vaporous aqueous stream from a liquid (aqueous) stream, such as a cyclone. Said means for separating a vaporous aqueous stream from a liquid (aqueous) stream is preferably situated in proximity to the blow tank, more preferably at the top of the blow tank.

The first vaporous aqueous stream usually comprises aqueous steam. The first vaporous stream can comprise minor amounts of volatile organic compounds, such as furfural, furfural derivatives, carboxylic acids, like acetic acid or formic acid, and methanol. The vaporous aqueous stream can additionally contain mineral acid species such as e.g. $SO_2$ or sulphurous acid or chlorine containing species, especially from optional acidic impregnation of the biomass in the pressurized reactor as discussed above. It is preferred that the amount of volatile organic compounds, such as furfural, furfural derivatives, carboxylic acids, like acetic acid or formic acid, methanol and/or mineral acid species in the first vaporous stream does not exceed 10.0 wt %, more preferably does not exceed 5.0 wt % and most preferably is in the range of from 0.1 to 2.5 wt %.

The vaporous stream is withdrawn from the blow tank, preferably separately from the aqueous slurry stream comprising the steam exploded biomass, preferably through a separate discharge port.

By means of withdrawing said first vaporous aqueous stream from the blow tank the absolute pressure in said blow tank is maintained above atmospheric pressure.

The first vaporous stream has the pressure as maintained in the blow tank. Consequently, the first vaporous stream has a certain temperature which is listed in the water vapour pressure table.

At atmospheric pressure water vapour has a temperature of 100° C.

At an absolute pressure of 2.0 bar (a) water vapour has a temperature of 120.2° C.

At an absolute pressure of 3.0 bar (a) water vapour has a temperature of 133.5° C.

At an absolute pressure of 4.0 bar (a) water vapour has a temperature of 143.6° C.

At an absolute pressure of 6.0 bar (a) water vapour has a temperature of 158.8° C.

At an absolute pressure of 8.0 bar (a) water vapour has a temperature of 170.4° C.

The first vaporous stream preferably has a temperature above 100° C., more preferably from 120° C. to 180° C., still more preferably from 130° C. to 175° C. and most preferably from 140° C. to 170° C., such as about 160° C.

The latent heat of the first vaporous aqueous stream is recovered. Thereby, the latent heat can be recovered by heat exchange to a stream of clean water. The heat exchange can for example be conducted by reboiling steam e.g. in a steam reboiler such as a tube and shell falling film reboiler, wherein the first vapour stream is condensed and a liquid stream of clean water is heated by means of the latent heat of condensation. The heated stream of clean water can be recycled in the method of the present invention. Said heated stream of clean water can either be a vaporous stream of clean water or a liquid stream of clean water. The vaporous stream of clean water can for example be used as steam in the step of thermally treating the biomass in the pressurized hydrolysis reactor.

Said means for recovering the latent heat from the first vaporous aqueous stream is preferably used as indirect heat exchanger for maintaining the pressure in the blow tank.

It is preferred that the pressure in the blow tank is maintained by means of a heat exchanger. The heat exchanger is preferably selected from an indirect heat exchanger, preferably a reboiler, such as a tube and shell falling film reboiler, or a direct heat exchanger, such as a condensing scrubber preferably equipped with a recycle cooler, more preferably from an indirect heat exchanger, preferably a reboiler, such as a tube and shell falling film reboiler.

For obtaining a pumpable slurry of steam exploded biomass, the steam exploded biomass in the blow tank is diluted with an aqueous diluent.

Said aqueous diluent is preferably obtained from a process downstream of the method for treating biomass according to the invention. Aqueous streams from downstream processes, which are suitable as aqueous diluent are e.g. a wash filtrate from enzymatic treatment or a condensate from ethanol rectification.

Generally, the temperature of said aqueous diluent is not important. The temperature of said aqueous diluent can be rather high.

The high temperature of the aqueous diluent is possible due to the evaporative cooling of the steam exploded biomass in the blow tank and the downstream cooling step in the flash tank. The temperature of said aqueous diluent is preferably in the range of from 45° C. to 100° C., more preferably from 45° C. to 90° C. and most preferably from 45° C. to 80° C.

In order to avoid further additional treatment steps of the pumpable slurry stream downstream from the flash tank for optimizing the slurry for enzymatic treatment one or more additional streams can be introduced into the blow tank.

For adjusting the pH of the pumpable slurry stream an alkaline solution can be introduced into the blow tank.

Thereby, the pH of the pumpable slurry stream is preferably adjusted to 4.0 to 6.5. A pH of 4.0 to 6.5 usually is the optimum pH for enzymatic hydrolysis.

Further, an aqueous solution comprising enzymes for saccharification of cellulose can be introduced into the blow tank.

In a preferred embodiment no alkaline solution and/or aqueous solution comprising enzymes for saccharification of cellulose is introduced into the blow tank. In said embodiment the aqueous slurry stream comprising the thermally treated biomass is optimized for enzymatic treatment by introducing an alkaline solution for adjusting the pH as discussed above and/or an aqueous solution comprising enzymes for saccharification of cellulose in the flash tank or downstream from the flash tank, if necessary.

The pumpable slurry stream discharged from the blow tank is introduced into a flash tank, wherein the absolute pressure in the flash tank is maintained below atmospheric pressure.

Preferably the absolute pressure in the flash tank is maintained below 0.5 bar(a), still more preferably below 0.3 bar(a) and most preferably from 0.01 to 0.25 bar(a).

It is preferred that the absolute pressure in the flash tank is adjusted and maintained to a certain absolute pressure in dependence of the temperature which shall be adjusted for the enzymatic hydrolysis. For example, for a temperature of 70° C. required in the enzymatic hydrolysis the pressure in the flash tank is adjusted and maintained at 0.3 bar (a), for a temperature of 50° C. required in the enzymatic hydrolysis the pressure in the flash tank is adjusted and maintained at 0.12 bar (a) or for a temperature of 32° C. required in the enzymatic hydrolysis the pressure in the flash tank is adjusted and maintained at 0.05 bar (a).

It is preferred that the aqueous slurry stream comprising the thermally treated biomass recovered from the blow tank is directly introduced into the flash tank.

Due to the pressure drop from the pressure maintained in the blow tank to the reduced pressure maintained in the flash tank evaporated water (blow steam) and hydrolyzed biomass are separated in the flash tank in two separate streams, a second vaporous aqueous stream and cooled aqueous slurry comprising the steam exploded biomass.

It is preferred that the two streams are separated by means for separating a second vaporous aqueous stream from a liquid (aqueous) stream, such as a cyclone. Said means for separating a second vaporous aqueous stream from a liquid (aqueous) stream is preferably situated in proximity to the flash tank, more preferably at the top of the flash tank.

The second vaporous aqueous stream usually comprises aqueous steam and volatile organic compounds, such as furfural, furfural derivatives, carboxylic acids, like acetic acid or formic acid, and methanol. The second vaporous aqueous stream can additionally contain mineral acid species such as e.g. $SO_2$ or sulphurous acid or chlorine containing species, especially from optional acidic impregnation of the biomass in the pressurized reactor as discussed above.

The second vaporous aqueous stream is withdrawn from the flash tank, preferably separately from the cooled aqueous slurry stream comprising the steam exploded biomass, preferably through a separate discharge port.

By means of withdrawing said second vaporous aqueous stream from the flash tank the absolute pressure in said flash tank is maintained below atmospheric pressure.

The withdrawn second vaporous aqueous stream is preferably at least partly condensed in means for condensing a vaporous aqueous stream.

The means for condensing a vaporous aqueous stream is preferably a condenser, such as a vertical tube and shell heat exchanger, into which the second vaporous aqueous stream can be introduced into the tubes and a coolant can be introduced on the shell side.

Said means for condensing a vaporous aqueous stream is preferably used as indirect heat exchanger for maintaining the pressure in the flash tank.

In the means for condensing a vaporous aqueous stream the withdrawn second vaporous aqueous stream is preferably separated into a third vaporous stream comprising methanol and a condensed stream comprising furfural and carboxylic acids.

As discussed above, the absolute pressure in the flash tank is preferably adjusted and maintained to a certain absolute pressure in dependence of the temperature which shall be adjusted for the enzymatic hydrolysis. As a consequence the cooled slurry stream comprising the steam exploded biomass discharged from the flash tank does not need to be further cooled before being treated with an enzyme.

An aqueous solution comprising enzymes for saccharification of cellulose can be introduced into the blow tank.

The cooled aqueous slurry stream comprising the steam exploded biomass discharged from the flash tank preferably is in the condition to be directly treated with an enzyme in an enzymatic hydrolysation step. It is preferred that the cooled aqueous slurry stream comprising the steam exploded biomass discharged from the flash tank is not subjected to a further cooling step or to a further pH adjusting step or both before being treated with an enzyme.

In certain embodiments, the amount of steam separated from the aqueous slurry comprising the thermally treated biomass in the first and second vaporous aqueous streams is rather high so that the solids concentration in the cooled aqueous slurry stream comprising the steam exploded biomass discharged from the flash tank is above 20 wt %, based on the total weight of the recovered aqueous slurry stream comprising the thermally treated biomass. In these cases the solids concentration in the cooled aqueous slurry stream comprising the steam exploded biomass discharged from the flash tank is adjusted to 5 to 20 wt %, based on the total weight of the discharged cooled aqueous slurry stream by introducing a liquid selected from water or an aqueous stream accrued in one of the process steps of the inventive method. It is thereby preferred that the diluting liquid has about the same temperature as the cooled aqueous slurry stream comprising the steam exploded biomass discharged from the flash tank.

It is preferred that the cooled aqueous slurry stream comprising the steam exploded biomass discharged from the flash tank has a temperature of from 40 to 80° C., more preferably of 40 to 75° C. and most preferably of from 40 to 60° C.

It is further preferred that the cooled aqueous slurry stream comprising the steam exploded biomass discharged from the flash tank has a pH of 4.0 to 6.5.

It is additionally preferred that the cooled aqueous slurry stream comprising the steam exploded biomass discharged from the flash tank has a solids concentration in the discharged cooled aqueous slurry stream of from 5 to 20 wt %, more preferably of from 10 to 20 wt %, and most preferably of from 15 to 20 wt %, based on the total weight of the discharged cooled aqueous slurry stream.

By enzymatic hydrolysis the carbohydrates such as cellulose in the biomass are hydrolyzed to mono- or oligosaccharides.

The method according to the invention is preferably operated in continuous mode.

Device

The present invention further relates to a device for treating biomass comprising
  a biomass feeding system;
  a pressurized reactor for thermally treating the biomass
  a blow tank;
  a discharging system for discharging the hydrolyzed biomass from the pressurized reactor to the blow tank by steam explosion;
  a flash tank; and
  a unit for enzymatically treating treated cooled aqueous slurry stream of biomass discharged from the flash tank;
wherein
the blow tank comprises
means for maintaining the absolute pressure in the blow tank above atmospheric pressure, preferably above 2 bar (a), still more preferably above 3 bar(a) and most preferably from 4 to 8 bar (a);
at least one injection port for injecting an aqueous diluent;
at least one discharge port for discharging a first vaporous aqueous stream;
at least one discharge port for discharging an aqueous slurry stream comprising the steam exploded biomass;
the flash tank comprises
means for maintaining the absolute pressure in the flash tank below atmospheric pressure, preferably below 0.5 bar (a), still more preferably below 0.3 bar(a) and most preferably from 0.01 to 0.25 bar (a);
at least one discharge port for discharging a second vaporous aqueous stream;
at least one discharge port for discharging a cooled aqueous slurry stream, and
the device further comprises a unit for recovering the latent heat from said first vaporous aqueous stream withdrawn from the blow tank.

The feeding system preferably comprises means for actively conveying the biomass into the pressurized reactor such as a screw feeder, e.g. a plug screw feeder optionally with a force feed screw feeding the plug screw feeder.

The pressurized reactor can comprise one or more such as one or two reactors.

In one embodiment the pressurized reactor comprises more than one reactor such as two reactors, e.g. an impregnation reactor and a hydrolysis reactor.

In another embodiment the pressurized reactor comprises only one reactor which suitably is a hydrolysis reactor.

The hydrolysis reactor can be a vertical hydrolysis reactor or a horizontal hydrolysis reactor.

For maintaining the pressure in the blow tank, the blow tank preferably is a system which is closed up to the atmosphere.

The at least one injection port for injecting the aqueous diluent is preferably connected to a feeding line for the aqueous diluent from an apparatus unit further downstream of the blow tank to the blow tank. Said feeding line can connect the at least one injection port for injecting the aqueous diluent with e.g. enzymatic treatment unit or a unit for ethanol rectification. Multiple injection port(s) can be situated over the whole length and width of the blow tank.

The blow tank can comprise at least one, such as one or multiple, injection port(s) for injecting an alkaline solution in order to adjust the pH of the discharged thermally treated aqueous slurry of biomass is adjusted to 4.0 to 6.5.

Multiple injection port(s) can be situated over the whole length and width of the blow tank. Still further, the blow tank can comprise at least one, such as one or multiple, injection port(s) for injecting an aqueous solution comprising enzymes for saccharification of cellulose. Multiple injection port(s) can be situated over the whole length and width of the blow tank. In a preferred embodiment the blow tank does not comprise injection port(s) for injecting an aqueous solution comprising enzymes for saccharification of cellulose.

The at least one discharge port for discharging aqueous slurry stream comprising the steam exploded biomass is preferably situated at the lower part of the blow tank.

The at least one discharge port for discharging the first vaporous aqueous stream is preferably situated at the upper part of the blow tank.

It is preferred that the means for maintaining the absolute pressure in the blow tank above atmospheric pressure, preferably above 2 bar (a), still more preferably above 3 bar(a) and most preferably from 4 to 8 bar (a) comprises a heat exchanger. The heat exchanger is preferably selected from an indirect heat exchanger, preferably a reboiler, such as a tube and shell falling film reboiler, or a direct heat exchanger, such as steam condenser or a condensing scrubber, preferably equipped with a recycle cooler. It is preferred that the heat exchanger is preferably selected from an indirect heat exchanger, preferably a reboiler, such as a tube and shell falling film reboiler.

The blow tank preferably further comprises means for agitating the thermally treated aqueous slurry of biomass introduced into a blow tank, such as mixer, e.g. an axial mixer.

The vapor space in the blow tank is preferably from 2 times to 8 times the vapor space of the pressurized reactor.

Still further, the device of the invention preferably comprises means for separating a vaporous stream from a liquid (aqueous) stream in the blow tank, such as a cyclone. Said means for separating a vaporous stream from a liquid (aqueous) stream is preferably situated in proximity to the blow tank, more preferably at the top of the blow tank.

The device further comprises unit for recovering the latent heat from said first vaporous aqueous stream withdrawn from the blow tank and preferably transferring the latent heat of condensation to a stream of clean water. Said means preferably is a heat exchanger such as a reboiler, preferably a tube and shell falling film reboiler.

Further, the device can comprise a feeding system for recirculating a vaporous stream of clean water to the pressurized reactor, preferably to the hydrolysis reactor.

For maintaining the reduced pressure in the flash tank, the flash tank preferably is a system which is closed up to the atmosphere.

The at least one discharge port for discharging the cooled aqueous slurry stream is preferably situated at the lower part of the flash tank.

The flash tank preferably further comprises at least one discharge port for discharging a second vaporous aqueous stream.

The at least one discharge port for discharging the second vaporous aqueous stream is preferably situated at the upper part of the flash tank.

It is preferred that the means for maintaining the absolute pressure in the flash tank below atmospheric pressure, preferably below 0.5 bar (a), still more preferably below 0.3 bar(a) and most preferably from 0.01 to 0.25 bar (a) comprises a heat exchanger, such as a condenser. The heat exchanger is preferably selected from an indirect heat exchanger, such as a tube and shell heat exchanger, or a direct heat exchanger, such as steam condenser or a condensing scrubber, preferably equipped with a recycle cooler. It is preferred that the heat exchanger is preferably selected from an indirect heat exchanger, such as a tube and shell heat exchanger.

The vapor space in the flash tank is preferably from 2 times to 8 times the vapor space of the pressurized reactor.

The vapor space in the blow tank is preferably from the same size to 5 times the vapor space of the flash tank.

Additionally, the device preferably comprises means for condensing the second vaporous aqueous stream downstream from the flash tank.

The means for condensing the second vaporous aqueous stream is preferably a condenser, such as a as a tube and shell heat exchanger.

Said means for condensing the second vaporous aqueous stream is preferably used as direct heat exchanger for maintaining the pressure in the flash tank.

Still further, the device preferably comprises means for transporting the pumpable slurry stream of biomass from the blow tank via the flash tank to the unit for enzymatic treatment, such as a pump.

Benefits of the Invention

The present invention provides an improved method and device for treating biomass in which a cooling step for cooling the thermally treated and discharged biomass to the optimum temperature for enzymatic hydrolysation is omitted.

Additionally, the method and device of the present invention provide an efficient reduction of toxic compounds, like carboxylic acids or furfural, which reduce the activity of enzymes and yeast in the enzymatic hydrolysis.

Still further, an efficient liquid management is provided by the method and device of the present invention, which improves energy management, reduces waste streams and handles gases, all in an environmentally friendly manner. Especially, an efficient recovery of energy in form of heat is provided by heat transfer from the first vaporous aqueous stream to a stream of clean water which can be recycled or otherwise used in the inventive method.

DETAILED DESCRIPTION OF THE FIGURES

Figure 1:
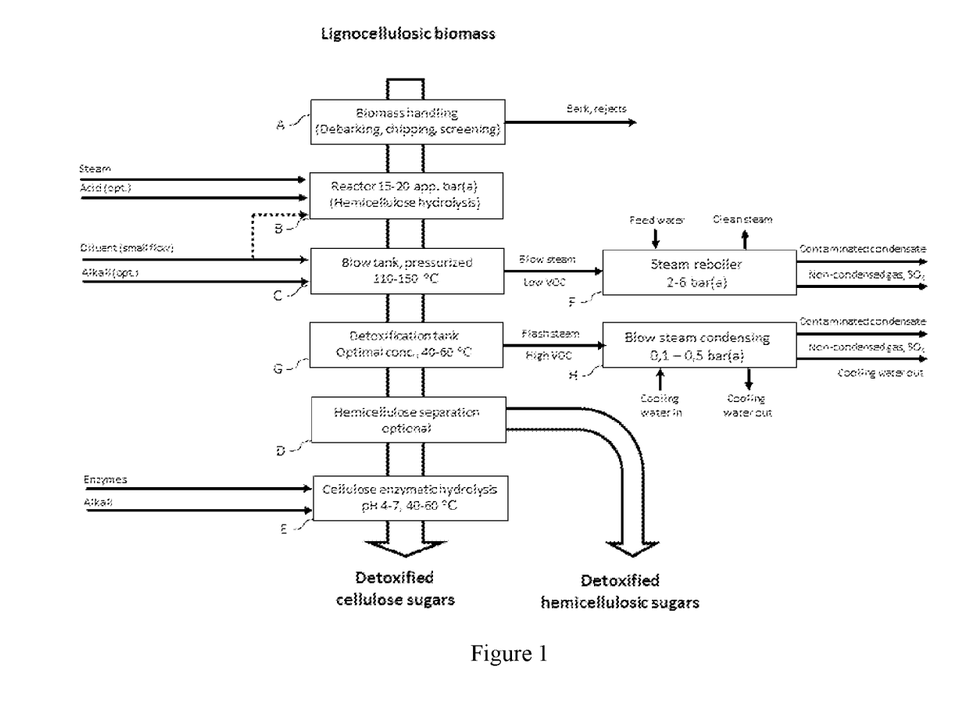
FIG. 1 exemplifies a typical biomass hydrolysis process.

FIG. 1 exemplifies a typical biomass pre-hydrolysis process of the prior art.

A lignocellulosic biomass of woody or agricultural origin is taken to a biomass handling step, A. The biomass is, if necessary de-barked, chipped or hammer-milled and screened for separation of harmful and inert solid material from biomass, for example gravel, stones metal particles and alike. Bark may also be separated as a reject. The biomass is then fed into the pre-hydrolysis step B by means of a feeding system. The feeding system preferably comprises means for conveying biomass into the reactor such as a screw feeder. The pressurized pre-hydrolysis step B may comprise one or multiple reactor shells connected in series or in parallel and they may be arranged vertically or horizontally. Vertical and horizontal pre-hydrolysis reactors are generally known in the art. The biomass is heated in the reactor(s) with direct steam to the required process temperature and pressure. The temperature is typically 170-215° C. and the pressure is in the range 10-25 bar. An acid may be added to step B to catalyze the hydrolysis reactions. The residence time of the biomass in the reactor unit is in the range of from 3 to 30 minutes. Hydrolyzed biomass is discharged, after completed hydrolysis reactions, through a blow valve or an orifice from the high pressure prevailing in the reactor to the atmospheric pressure prevailing in the blow tank, step C. The pressure-drop over the blow valve or orifice is high which results in efficient defibration of the biomass and opens the fiber structure making good access for chemicals and enzymes in downstream hydrolysis steps. The temperature of the hydrolyzed biomass drops rapidly at the discharge as water and volatile material evaporate to the equilibrium temperature which is about 100° C. Such a discharge with a sudden pressure drop over a restriction is also called "steam explosion" discharge. Evaporated water, blow steam which also contains some volatile hydrocarbons, is evacuated from the blow tank to a condensing system, step F. Condensed blow steam from step F is sent to a waste water treatment system and non-condensed gas to exhaust gas handling system. The hydrolyzed biomass which is discharged to the blow tank will equilibrate around 100° C. which is too high for down-stream enzymatic hydrolysis and it is not pumpable. Enzymes typically works effectively in the temperature range 40-60° C. Known prior art proposes cooling and dilution of the biomass by mixing with an aqueous coolant. Such a dilution with a coolant may take place in the blow tank as indicated in FIG. 1 or (possibly) in another container located downstream after the blow tank. In some cases, is coolant added upstream the blow valve or orifice (to step B). This is sometimes denoted "dilution discharge" since the liquid vaporization over the blow valve or orifice is reduced due to the cooling effect. The pre-hydrolyzed slurry from step C, is pumped to step E for enzymatic hydrolysis. An optional step D, may be installed before step E. Dissolved hemicellulose sugars are washed in step D with a drum-washer, screw-press or alike and are treated separately from cellulose containing wet solid phase which is transported to said step E for enzymatic treatment. The solid phase is in such case diluted again to a consistency suitable for enzymatic hydrolysis. A batch type process, comprising one (or multiple reactors) is typical, which means the feed of material to step B and the discharge of material from said step B are discontinuous, but step B may be designed and operated in a continuous mode as well.

The draw-back of the process in FIG. 1 is that the dilution in step C (and step B if used), for achieving 40-60° C. slurry temperature, may be such that the consistency of the slurry is very low, resulting in a very high volumetric process (diluted slurry) flow. High volumetric flow will result in very large reactor (tank) sizes for enzymatic hydrolysis and fermentation. The diluted slurry also contains compounds, which are toxic and may be harmful for enzymes and yeast since the evaporative cooling to step C only reach 100° C. Too low slurry concentration increases operating expenditures since water will be separated mechanically or thermally somewhere in a downstream process step, such as fractionation, evaporation and drying.

Figure 2:
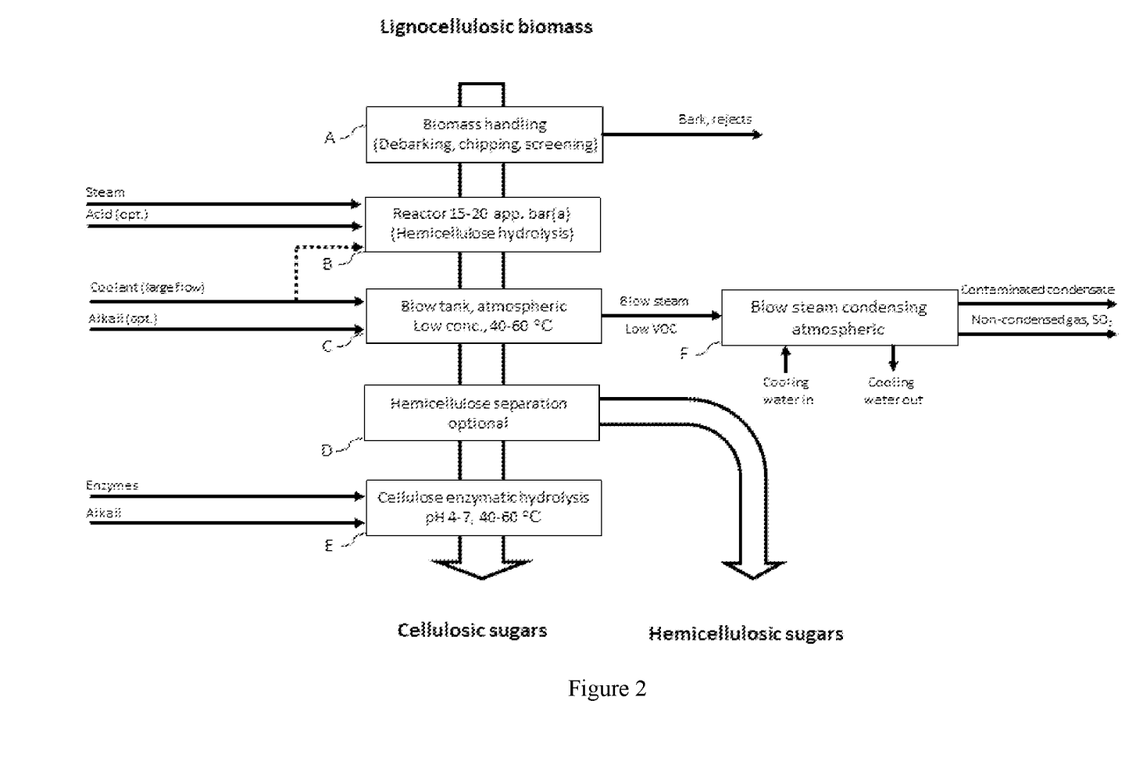
FIG. 2 shows a schematic overview of biomass hydrolysis according to the present invention.

FIG. 2 exemplifies schematically an embodiment of biomass hydrolysis according to the present invention.

The difference to prior art, as exemplified in FIG. 1 is that the blow tank, step C, is sealed and it is operated above atmospheric pressure. The pressure in the blow tank is maintained by means of an indirect heat exchanger, in the range 2 to 8 bar (a). The heat exchanger, step F, is preferably a falling film steam reboiler, preferably a shell and tube heat exchanger with condensing steam inside the tubes and clean, boiling feed-water on the shell side but indirect reboilers of other designs may be used as well. The reboiler produces clean, saturated low-pressure steam which is used in adjacent process departments for example for heating, fractionation, drying or alike. Contaminated condensate from the reboiler is preferably not recycled to the blow tank as it contains compounds toxic for downstream enzymatic and fermentation processes. The condensate is treated at a waste water plant optionally including recovery of toxic compounds, for example furfural, as a useful chemical. The tail-gas is burned or treated in a scrubber since it is malodorous. The hydrolyzed biomass is now diluted to a pumpable slurry in the blow tank to any required consistency. The temperature of the slurry is in range 120 to 170° C. determined by the absolute pressure prevailing blow tank. It is a feature of our invention that hot (un-cooled) condensate may be used as a diluent since the temperature of the slurry is determined by the pressure in the blow tank. Heat exchangers for cooling of the diluent are no longer required which give savings of both capital and operating expenditures. The slurry is too hot for downstream process steps and it is so cooled evaporatively to required temperature in a flash-tank, step G. The pressure in the flash-tank is maintained with a condenser (H), which is preferably an indirect shell and tube heat-exchanger with condensing steam inside the tubes and coolant on the shell side. Other types of condensers may be used as well. The absolute pressure in the flash-tank is maintained below atmospheric pressure, preferably below 0.5 bar (a), still more preferably below 0.3 bar(a) and most preferably from 0.01 to 0.25 bar (a). Evaporative cooling may now proceed to 40-60° C. in the flash tank i.e. to a temperature which is favorable, for example, for enzymatic hydrolysis. In other words, the present invention adds one more degree of freedom for optimizing the conditions for enzymatic hydrolysis. The flow of diluent is controlled independently of temperature requirement of the slurry which will result in small reactor (tank) sizes for enzymatic hydrolysis and fermentation thus reducing investment costs. The evaporative cooling in the flash-tank, step G, has a detoxification effect on the slurry. Steam evaporate from biomass thereby introducing a stripping effect which efficiently desorbs furfural, acetic acid, formic acid and other hydrocarbons alike to the vapor phase. The resulting slurry from the flash-tank (G) has a reduced content of toxic compounds which results in better yield in downstream hydrolysis and fermentation. The partial vaporization of carboxylic acids results in a lower usage of alkali for pH adjustment as well. As said, an acid may be used in catalyzing hydrolysis in step B. The catalyst may be a mineral acid but also $SO_2$ or sulphurous acid. The present invention will reduce the concentration of $SO_2$ or sulphurous acid in the slurry in the case such catalysts are used, thereby reducing the requirement of alkali for neutralization. The method according to the invention is preferably operated in continuous mode.

Figure 3:
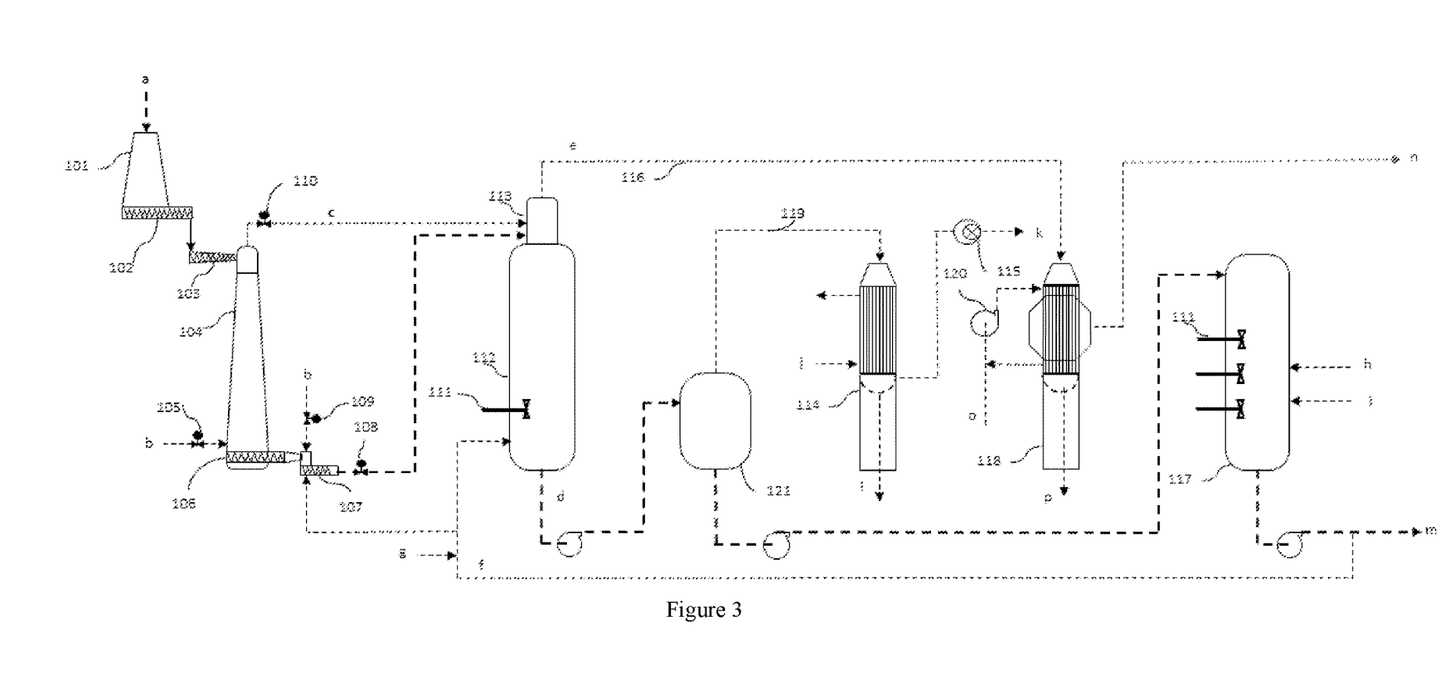
FIG. 3 shows a detailed example of biomass hydrolysis according to the present invention.

FIG. 3 shows a schematic overview of the method and device of the present invention. Lignocellulosic biomass (a), for example wood, bark, bagasse and straw, is fed to a receiving bin 101 which equalizes variations in raw material flow and provides a sufficient volume for a stable material supply to the feeding screws 102 and 103. The raw material (a) to the bin 101 is split up to chips, flakes or splinters and it may be screened for removal of unwanted components such as sand or gravel which can cause wear and blockages in downstream machineries. The biomass is normally not dried, and it has a typical moisture content in the range of 30-50%. But, this not a limitation, the next process step, the thermal treatment step (steam explosion step) works well with dry material, down to approximately 10% of moisture and but also with a material having a moisture above 50%. The bin 101 is operated at atmospheric pressure but the thermal treatment reactor 104 operates at elevated temperature, 170-215° C., and pressure, 10-25 bar(a). The screw 102, which is operated essentially at atmospheric pressure, provides a constant flow of biomass to the next screw, 103. Screw 103, also denoted "plug-screw", is conical and it compresses to biomass to a hard plug such that the high pressure in the reactor 104 is sealed to atmospheric pressure. Both screws work continuously and the hard pressure sealing biomass plug formed in screw 103 is mechanically disintegrated when it exits to the reactor 104. Steam (b), is added to the reactor for heating the and hydrolyzing the biomass. Hemicelluloses of the biomass are easily hydrolyzed at the high temperature prevailing in the reactor forming sugar oligomers and monomers. A part of the sugars released will dehydrate to furfural and hydroxymethyl furfural which are unwanted in downstream fermentation processes. Also, other volatile by products are formed and released from the biomass, such as acetic acid, formic acid and methanol. Sulphuric acid or sulphurous acid may be added to the process for catalyzing hydrolysis. The acid may be added directly to the biomass in the reactor 104, but it is possible to add it before the screw 103 in dedicated mixing screws or soaking systems (not shown in FIG. 3). Alternatively, sulphur dioxide gas may be added as catalyst, either to the reactor 104, but preferably to a mixing or soaking system upstream plug screw 103. Biomass containing hydrolysate is emptied from the reactor 104 with a screw and/or a scraper, 106, which is in the bottom. The biomass is discharged to a blow tank 112 through a blow valve with an adjustable aperture or a fixed orifice, 108. The reactor system is operated continuously, the feeding of biomass material to the reactor 104 and discharge of material from it are both essentially continuous such that the level and retention time in the reactor remains constant. The blow tank, 112, is operated above atmospheric pressure (above 1.01 bar(a)). The pressure-drop over valve 108 is very high since the upstream pressure is 10-25 bar. The high pressure-drop over the valve results in a "steam explosion" by which is meant that water evaporates in the pores and cavities of the biomass when pressure rapidly decreases, thereby expanding and destroying the biomass material structure. The result of steam explosion is an open material structure suitable for down-stream enzymatic hydrolysis. A rotating mixer or screw, 107, may be installed upstream the blow valve 108, for assisting of the discharge of biomass through the blow valve or a discharge orifice. Further, steam (b) is added to said mixer, 107, for helping discharge of biomass through the blow valve. Hydrolyzed biomass is collected to the blow tank, 112 which is operated above the atmospheric pressure, 1.01 bar(a), for example at an absolute pressure of 6 bar(a). The blow tank is sealed to ambient atmosphere such that the overpressure steam cannot leak to environment. Biomass and hydrolysate may be separated with a cyclonic part, 113 installed at the top of the blow tank. The biomass inlet to the blow tank is tangential and the diameter of the top part is selected such that a high tangential velocity is reached for good separation of steam and biomass. The pressure in the blow tank is controlled with a blow steam condensing system comprising a reboiler 118. Blow steam, (e), is a mixture of steam originating from the pre-treatment reactor 104 and steam obtained from water and volatile hydrocarbons which evaporate from moist hydrolyzed biomass. Blow steam, having a temperature of about 150° C. at a absolute pressure of about 6 bar(a), is conducted with a pipe 116 to the reboiler 118. The reboiler 118 is preferably a vertical tube and shell falling film heat exchanger with the blow steam inside the tubes and a feed water being circulated by pump 120 on the shell side. The circulating stream of feed water is heated in the reboiler 118 by the latent heat of the condensed blow stream to such an extent that the stream of clean water is evaporated to produce clean low pressures steam which may be used for example in a downstream process such as rectification of ethanol or stripping of contaminated condensates or drying of fodder yeast. Blow steam condensate (p), contaminated with condensable hydrocarbons, is collected in the bottom part of the reboiler and is pumped to other process steps for recovery of chemicals and/or effluent treatment system. The biomass is diluted to a pumpable slurry by mixing, for example hydrolysate (f) from downstream process steps 117 to the blow tank. Dilution liquid may be added also upstream the blow valve 107, if a "dilution blow" discharge is preferred. Dilution of biomass in/to the blow-tank may also be achieved by replacing recycle hydrolysate partly or wholly with another suitable recycle condensate and/or water (g). The temperature of the diluent is not important, it may be hot because it is still evaporatively cooled (or heated) in the blow tank to the equilibrium temperature. This is one benefit of the invention as heat exchangers for diluent cooling are not required. Mixing may be assisted with wall mounted axial mixer(s), 111. In the same manner is acidity adjusted by adding a suitable caustic solution to the blow tank 112 or to the dilution liquid (g). As said above, the hydrolysis process in reactor 104 releases in parallel with hemicellulose sugars several volatile hydrocarbons, some of which are unwanted in enzymatic hydrolysis and fermentation. Only a fraction of these hydrocarbons will evaporate with blow steam since the blow tank is pressurized. The diluted slurry from the blow tank, 112 is next introduced into a flash tank, 121, which is operated below the atmospheric pressure, 1.01 bar(a). The flash-tank is sealed to ambient atmosphere such that air cannot leak into it. The purpose of the flash tank is to evaporatively cool and de-toxify the hot slurry from the blow tank 112 making it suitable for downstream processes, for example enzymatic hydrolysis. Enzymes typically require a temperature in the range 40-60° C. for good activity. The biomass inlet to the flash tank is tangential and the diameter of the top part is selected such that a high tangential velocity is reached for good separation of steam and slurry. The pressure in the flash tank is controlled with an indirect condenser, 114. The condenser 114 is preferably a vertical tube and shell heat exchanger with the flash steam inside the tubes and a coolant (j) on the shell side. Flash steam condensate (l), contaminated with condensable hydrocarbons, is collected in the bottom part of the condenser and is pumped to other process steps for recovery of chemicals and/or effluent treatment system. The flash steam contains also non-condensable gases (k) which are evacuated from the condenser by means of a vacuum pump, 115, preferably a liquid ring pump. The chemicals contained in the non-condensable gas (k) may be recovered with an absorption tower or the gas is burned for example in a torch or a nearby boiler. The (total) pressure in the flash tank 121 is so low that the biomass slurry is evaporatively cooled to a temperature which is suitable in down-stream enzymatic hydrolysis 117. For example, the pressure in the blow tank is adjusted to 12 kPa if 50° C. was required in the enzymatic step. Most of the moisture in the biomass is water so the steam pressure is approximately follows that of pure water corrected with the boiling point elevation caused by dissolved hemicellulose sugars. The cooled and detoxified slurry is pumped to reactor 117 for enzymatic hydrolysis. As said above, the hydrolysis process in reactor 104 release in parallel with hemicellulose sugars several components, some of which are unwanted in enzymatic hydrolysis and fermentation. According to our invention is biomass and hydrolysate cooled evaporatively in two stages to a relatively low temperature. In known steam explosion processes is biomass cooled (evaporatively at pressure release) from for example 200° C. to 100° C., but according to our invention is evaporative cooling performed from 200° C. to about 50° C. in two stages. The water evaporation thus increases with 50% in this example which results in more thorough desorption of volatile (unwanted) hydrocarbon compounds. The hydrolysate from the flash tank 119 contains lower concentration of harmful toxic compounds in comparison to prior art and this way will enzymatic hydrolysis downstream work better. The evaporated water from the blow tank 112 having a temperature of more than 100° C., such as 150° C. at an absolute pressure of 6 bar(a), is used to heat feed water, thus efficiently recovering energy from the process as clean low-pressure steam.

The invention claimed is:
1. A method in a continuous mode, the method comprising the steps of
   (a) feeding lignocellulosic biomass to a pressurized reactor;
   (b) supplying steam to the pressurized reactor and at least partially condensing said steam in the pressurized reactor, wherein the pressure in the pressurized reactor is 5 bar(a) to 35 bar(a);
   (c) hydrolysing hemicellulose sugars of said biomass with said at least partially condensed steam in the pressurized reactor, thereby obtaining a hydrolysed biomass;
   (d) discharging said hydrolyzed biomass from the pressurized reactor into a blow tank by steam explosion to produce a steam exploded biomass;
   (e) diluting the steam exploded biomass in the blow tank with an aqueous diluent to a pumpable aqueous slurry; withdrawing a first vaporous aqueous stream from the blow tank for maintaining the absolute pressure in the blow tank above 2 bar(a); and recovering the latent heat from the first vaporous aqueous stream;
   (f) pumping said aqueous slurry from the blow tank to a flash-tank and withdrawing a second vaporous aqueous stream from the flash tank for evaporative cooling to produce a cooled aqueous slurry and for maintaining the absolute pressure in the flash-tank below 0.5 bar(a);
   (g) discharging the cooled aqueous slurry from the flash tank as discharged cooled aqueous slurry stream; and
   (h) treating the discharged cooled aqueous slurry stream with an enzyme.

2. The method of claim 1, wherein the pressure in the blow tank is maintained by means of a heat exchanger, which is selected from the group consisting of an indirect heat exchanger and a direct heat exchanger.

3. The method of claim 1, wherein the pressure in the flash tank is maintained by means of a heat exchanger, which is selected from the group consisting of an indirect heat exchanger and a direct heat exchanger.

4. The method of claim 1, wherein the pressure in the flash tank is maintained below 0.3 bar(a).

5. The method of claim 1, wherein the pressure in the flash tank is maintained at from 0.01 bar(a) to 0.25 bar(a).

6. The method of claim 1, wherein the aqueous diluent is obtained from a downstream process.

7. The method of claim 1, wherein the pH of the pumpable slurry is adjusted to 4.0 to 6.5 by introducing an alkaline solution into the blow tank.

8. The method of claim 1, wherein the solids concentration in the pumpable slurry in the blow tank is adjusted to 10 wt % to 20 wt %, based on the total weight of the pumpable slurry.

9. The method of claim 1, wherein an aqueous solution comprising enzymes for saccharification of cellulose is introduced into the flash tank.

10. The method of claim 1, wherein the discharged cooled aqueous slurry has a temperature of from 40° C. to 80° C.

11. The method of claim 1, wherein the first vaporous stream withdrawn from the blow tank comprises water vapor, furfural, carboxylic acids and methanol and/or the second vaporous stream withdrawn from the flash tank comprises water vapor, furfural, carboxylic acids and methanol.

12. The method of claim 1, wherein the hydrolyzed biomass in the pressurized reactor has a temperature of from 120° C. to 250° C. before being discharged by steam explosion into the blow tank.

13. The method of claim 2, wherein the heat exchanger is a reboiler.

14. The method of claim 13, wherein the reboiler is a tube and shell falling film reboiler.

15. The method of claim 2, wherein the heat exchanger is a condensing scrubber.

16. The method of claim 15, wherein the condensing scrubber is equipped with a recycle cooler.

17. The method of claim 3, wherein the heat exchanger is a tube and shell heat exchanger.

18. The method of claim 3, wherein the heat exchanger is a condensing scrubber.

19. The method of claim 18, wherein the condensing scrubber is equipped with a recycle cooler.

20. The method of claim 1, wherein the pressure in the blow tank is maintained at from 4 bar(a) to 8 bar(a).

* * * * *